US012001584B2

(12) United States Patent
Ratliff et al.

(10) Patent No.: US 12,001,584 B2
(45) Date of Patent: Jun. 4, 2024

(54) PRIVACY-PRESERVING CONTACT TRACING

(71) Applicant: Raytheon BBN Technologies Corp., Cambridge, MA (US)

(72) Inventors: Zachary Ratliff, Somerville, MA (US); Joud Khoury, Boston, MA (US)

(73) Assignee: RAYTHEON BBN TECHNOLOGIES CORP., Cambridge, MA (US)

( * ) Notice: Subject to any disclaimer, the term of this patent is extended or adjusted under 35 U.S.C. 154(b) by 323 days.

(21) Appl. No.: 17/326,498

(22) Filed: May 21, 2021

(65) Prior Publication Data
US 2021/0365585 A1 Nov. 25, 2021

Related U.S. Application Data

(60) Provisional application No. 63/028,904, filed on May 22, 2020.

(51) Int. Cl.
| | |
|---|---|
| *G06F 21/62* | (2013.01) |
| *G16H 10/60* | (2018.01) |
| *H04L 9/06* | (2006.01) |
| *H04L 9/32* | (2006.01) |

(52) U.S. Cl.
CPC ......... *G06F 21/6245* (2013.01); *G16H 10/60* (2018.01); *H04L 9/0643* (2013.01); *H04L 9/3218* (2013.01); *H04L 9/3247* (2013.01)

(58) Field of Classification Search
None
See application file for complete search history.

(56) References Cited

U.S. PATENT DOCUMENTS 10,887,104 B1 * 1/2021 Jayachandran ....... H04L 9/3239

OTHER PUBLICATIONS

Canetti; Ran et al. "Anonymous Collocation Discovery: Harnessing Privacy to Tame the Coronavirus" [online] Arxiv, Apr. 7, 2020 [retrieved May 20, 2023]. Retrieved from the Internet: URL: https://arxiv.org/pdf/2003.13670.pdf (Year: 2020).*
Ben-Sasson; Eli et al. "Scalable Zero Knowledge via Cycles of Elliptic Curves" [online] IACR, Sep. 18, 2016 [retrieved May 20, 2023]. Retrieved from the Internet: URL: https://eprint.iacr.org/2014/595.pdf (Year: 2016).*

(Continued)

*Primary Examiner* — Taghi T Arani
*Assistant Examiner* — Joshua Raymond White
(74) *Attorney, Agent, or Firm* — CANTOR COLBURN LLP

(57) ABSTRACT

Techniques for privacy-preserving contact tracing are disclosed, including: generating, by a first user device, a first proximity token for contact tracing; receiving, by the first user device, a second proximity token from a second user device; generating, by the first user device, a hash based on the first proximity token and the second proximity token; generating, by the first user device using a prover function of a preprocessing zero knowledge succinct non-interactive argument of knowledge (pp-zk-SNARK), a cryptographic proof attesting that an individual associated with the first user device tested positive for a pathogen; and transmitting, by the first user device, publicly verifiable exposure data including at least the cryptographic proof and the hash to a public registry.

14 Claims, 5 Drawing Sheets

(56) References Cited

OTHER PUBLICATIONS

Dijour; Dean "NOVID: Anonymous Contact Tracing with Ultrasound" [online] Wevolver, May 12, 2020 [retrieved May 20, 2023]. Retrieved from the Internet. URL: https://www.wevolver.com/article/novid.anonymous.contact.tracing.with.ultrasound (Year: 2020).*

Xie; Tiancheng et al. "Libra: Succinct Zero-Knowledge Proofs with Optimal Prover Computation" [onlines] IACR, Dec. 24, 2019 [retrieved May 20, 2023]. Retrieved from the Internet: URL: https://eprint.iacr.org/archive/2019/317/1577169751.pdf (Year: 2019).*

Liu; Joseph et al. "Privacy-Preserving COVID-19 Contact Tracing App: A Zero-Knowledge Proof Approach" [online] IACR, May 6, 2020 [retrieved May 20, 2023]. Retrieved from the Internet: URL: https://eprint.iacr.org/archive/2020/528/1588772633.pdf (Year: 2020).*

Trieu; Ni et al. "Epione: Lightweight Contact Tracing with Strong Privacy" [online] arxiv, May 2, 2020 [retrieved May 20, 2023]. Retrieved from the Internet: URL: https://arxiv.org/pdf/2004.13293.pdf (Year: 2020).*

Chiesa; Alessandro et al. "Marlin: Preprocessing zkSNARKs with Universal and Updatable SRS" [online] IACR, Jan. 1, 2020 [retrieved May 20, 2023]. Retrieved from the Internet: URL: https://eprint.iacr.org/archive/2019/1047/1577913438.pdf (Year: 2020).*

Groth, Jens "On the Size of Pairing-base Non-interactive Arguments" [online] IACR, May 31, 2016 [retrieved May 20, 2023]. Retrieved from the Internet: URL: https://eprint.iacr.org/2016/260.pdf (Year: 2016).*

Ratliff Zachary et al: 11 zkSNARKs to the rescue: proof-of-contact in zero knowledge, arXiv, Jun. 7, 2020 (Jun. 7, 2020), XP055840397, Retrieved from the Internet: URL:https://arxiv.org/pdf/2005.12676v3.pdf.

Jean-Franois Biasse et al: Trace-Sigma: 1-15 a privacy-preserving contact tracing app, IACR, International Association for Cryptologic Research vol. 20200627:185311, Jun. 25, 2020 (Jun. 25, 2020), pp. 1-7, XP061036046, Retrieved from the Internet: URL:http://eprint.iacr.org/2020/792.pdf.

Joseph K Liu et al: Privacy-Preserving COVID-19 Contact Tracing App: A Zero-Knowledge Proof Approach , IACR, International Association for Cryptologic Research, vol. 20200506:134353, May 6, 2020 (May 6, 2020), pp. 1-22, XP061035809, Retrieved from the Internet: URL:http://eprint.iacr.org/2020/528.pdf.

Hannah Alsdurf et al: "COVI White Paper", 1-15 arxiv.org, Cornell University Library, 201 Olin Library Cornell University Ithaca, NY, 14853, May 18, 2020 (May 18, 2020), XP081671734, pp. 8,23, pp. 35-42.

Ye Xia et al: "How to Return to Normalcy: 1-15 Fast and Comprehensive Contact Tracing of COVID-19 through Proximity Sensing Using Mobile Devices", arxiv.org, Cornell University Library, 201 Olin Library Cornell University Ithaca, NY, 14853, Apr. 27, 2020 (Apr. 27, 2020), XP081653309, section IV-C.

Xueping Peng et al: "Temporal 1-15 Self-Attention Network for Medical Concept Embedding", arxiv.org, Cornell University Library, 201 Olin Library Cornell University Ithaca, NY, 14853, Sep. 15, 2019 (Sep. 15, 2019), XP081477605.

European Search Report for application EP21182938 dated Nov. 18, 2021.

* cited by examiner

PRIVACY-PRESERVING CONTACT TRACING

CROSS REFERENCE TO RELATED APPLICATIONS

This application claims priority under 35 USC § 119(e) to U.S. Provisional Patent Application Ser. No. 63/028,904, titled "CRYPTOGRAPHIC PROTOCOL FOR PRIVACY-PRESERVING CONTACT TRACING," filed May 22, 2020, which is hereby incorporated by reference in its entirety.

BACKGROUND

Contact tracing refers to techniques for identifying individuals who have been in contact with somebody infected with a virus, bacteria, or other pathogen. For example, contact tracing has been used to identify and notify individuals who have come in close contact with people infected with severe acute respiratory syndrome coronavirus 2 (SARS-CoV-2), the virus that causes coronavirus disease 2019 (COVID-19). Contact tracing may also be used for tuberculosis, measles, human immunodeficiency virus (HIV), Ebola, influenza, and many other pathogens. In general, contact tracing can help stop the spread of a pathogen, provide testing and/or other medical services for those who might not know they were exposed to the pathogen, and obtain data for epidemiology research relating to the pathogen. However, the value of contact tracing must be balanced against the privacy concerns of the individuals being traced.

Approaches described in this section have not necessarily been conceived and/or pursued prior to the filing of this application. Accordingly, unless otherwise indicated, approaches described in this section should not be construed as prior art.

TECHNICAL FIELD

The present disclosure relates generally to contact tracing for pathogens.

SUMMARY

In general, in one aspect, one or more non-transitory computer-readable media store instructions that, when executed by one or more processors, cause the one or more processors to perform operations including: generating, by a first user device, a first proximity token for contact tracing; receiving, by the first user device, a second proximity token from a second user device; generating, by the first user device, a first hash based on the first proximity token and the second proximity token; generating, by the first user device using a prover function of a preprocessing zero knowledge succinct non-interactive argument of knowledge (pp-zk-SNARK), a first cryptographic proof attesting that a first individual associated with the first user device tested positive for a pathogen; and transmitting, by the first user device, first publicly verifiable exposure data including at least the first cryptographic proof and the first hash to a public registry.

The operations may further include: receiving, by the second user device, the first proximity token from the first user device; generating, by the second user device, the first hash based on the first proximity token and the second proximity token; determining, by the second user device, that the public registry includes the first hash; responsive to determining that the public registry includes the first hash, checking the first cryptographic proof using a verifier function of the pp-zk-SNARK; and based at least on checking the first cryptographic proof, determining that a second individual associated with the second user device had contact with the first individual. The operations may further include: generating, by the second user device, a second hash based on proximity tokens from the second user device and a third user device; generating, by the second user device using the prover function of the pp-zk-SNARK, a second cryptographic proof attesting that the second individual had contact with the first individual; transmitting, by the second user device, second publicly verifiable exposure data including at least the second cryptographic proof and the second hash to the public registry. The operations may further include: generating, by the third user device, the second hash based on the proximity tokens from the second user device and the third user device; determining, by the third user device, that the public registry includes the second hash; responsive to determining that the public registry includes the second hash, checking the second cryptographic proof using the verifier function of the pp-zk-SNARK; and based at least on checking the second cryptographic proof, determining that a third individual associated with the third user device had second-order contact with the first individual.

The operations may further include: generating an alert indicating that the second user device had contact with the first individual. The operations may further include: obtaining, by the first user device, a signature based on a private signing key from a healthcare provider, the first publicly verifiable exposure data further including the signature. The second user device may be associated with a shared space and used for surface-based contact tracing.

In general, in one aspect, a system includes at least one device including a hardware processor. The system is configured to perform operations including: generating, by a first user device, a first proximity token for contact tracing; receiving, by the first user device, a second proximity token from a second user device; generating, by the first user device, a first hash based on the first proximity token and the second proximity token; generating, by the first user device using a prover function of a preprocessing zero knowledge succinct non-interactive argument of knowledge (pp-zk-SNARK), a first cryptographic proof attesting that a first individual associated with the first user device tested positive for a pathogen; and transmitting, by the first user device, first publicly verifiable exposure data including at least the first cryptographic proof and the first hash to a public registry.

The operations may further include: receiving, by the second user device, the first proximity token from the first user device; generating, by the second user device, the first hash based on the first proximity token and the second proximity token; determining, by the second user device, that the public registry includes the first hash; responsive to determining that the public registry includes the first hash, checking the first cryptographic proof using a verifier function of the pp-zk-SNARK; and based at least on checking the first cryptographic proof, determining that a second individual associated with the second user device had contact with the first individual. The operations may further include: generating, by the second user device, a second hash based on proximity tokens from the second user device and a third user device; generating, by the second user device using the prover function of the pp-zk-SNARK, a second cryptographic proof attesting that the second individual had contact with the first individual; transmitting, by the second user device, second publicly verifiable exposure data including at least the second cryptographic proof and the second hash to the public registry. The operations may further include: generating, by the third user device, the second hash based on the proximity tokens from the second user device and the third user device; determining, by the third user device, that the public registry includes the second hash; responsive to determining that the public registry includes the second hash, checking the second cryptographic proof using the verifier function of the pp-zk-SNARK; and based at least on checking the second cryptographic proof, determining that a third individual associated with the third user device had second-order contact with the first individual.

The operations may further include: generating an alert indicating that the second user device had contact with the first individual. The operations may further include: obtaining, by the first user device, a signature based on a private signing key from a healthcare provider, the first publicly verifiable exposure data further including the signature. The second user device may be associated with a shared space and used for surface-based contact tracing.

In general, in one aspect, a method includes: generating, by a first user device, a first proximity token for contact tracing; receiving, by the first user device, a second proximity token from a second user device; generating, by the first user device, a first hash based on the first proximity token and the second proximity token; generating, by the first user device using a prover function of a preprocessing zero knowledge succinct non-interactive argument of knowledge (pp-zk-SNARK), a first cryptographic proof attesting that a first individual associated with the first user device tested positive for a pathogen; and transmitting, by the first user device, first publicly verifiable exposure data including at least the first cryptographic proof and the first hash to a public registry.

The method may further include: receiving, by the second user device, the first proximity token from the first user device; generating, by the second user device, the first hash based on the first proximity token and the second proximity token; determining, by the second user device, that the public registry includes the first hash; responsive to determining that the public registry includes the first hash, checking the first cryptographic proof using a verifier function of the pp-zk-SNARK; and based at least on checking the first cryptographic proof, determining that a second individual associated with the second user device had contact with the first individual. The method may further include: generating, by the second user device, a second hash based on proximity tokens from the second user device and a third user device; generating, by the second user device using the prover function of the pp-zk-SNARK, a second cryptographic proof attesting that the second individual had contact with the first individual; transmitting, by the second user device, second publicly verifiable exposure data including at least the second cryptographic proof and the second hash to the public registry. The method may further include: generating, by the third user device, the second hash based on the proximity tokens from the second user device and the third user device; determining, by the third user device, that the public registry includes the second hash; responsive to determining that the public registry includes the second hash, checking the second cryptographic proof using the verifier function of the pp-zk-SNARK; and based at least on checking the second cryptographic proof, determining that a third individual associated with the third user device had second-order contact with the first individual.

The method may further include: generating an alert indicating that the second user device had contact with the first individual. The method may further include: obtaining, by the first user device, a signature based on a private signing key from a healthcare provider, the first publicly verifiable exposure data further including the signature. The second user device may be associated with a shared space and used for surface-based contact tracing.

One or more embodiments described in this Specification and/or recited in the claims may not be included in this General Overview section.

BRIEF DESCRIPTION OF THE DRAWINGS

Various aspects of at least one embodiment are discussed below with reference to the accompanying Figures, which are not intended to be drawn to scale. The Figures are included to provide illustration and a further understanding of the various aspects and embodiments, and are incorporated in and constitute a part of this specification, but are not intended to define the limits of the disclosure. In the Figures, each identical or nearly identical component that is illustrated in various Figures is represented by a like numeral. For the purposes of clarity, some components may not be labeled in every figure. In the Figures.

DETAILED DESCRIPTION

I. Introduction

Figure 1:
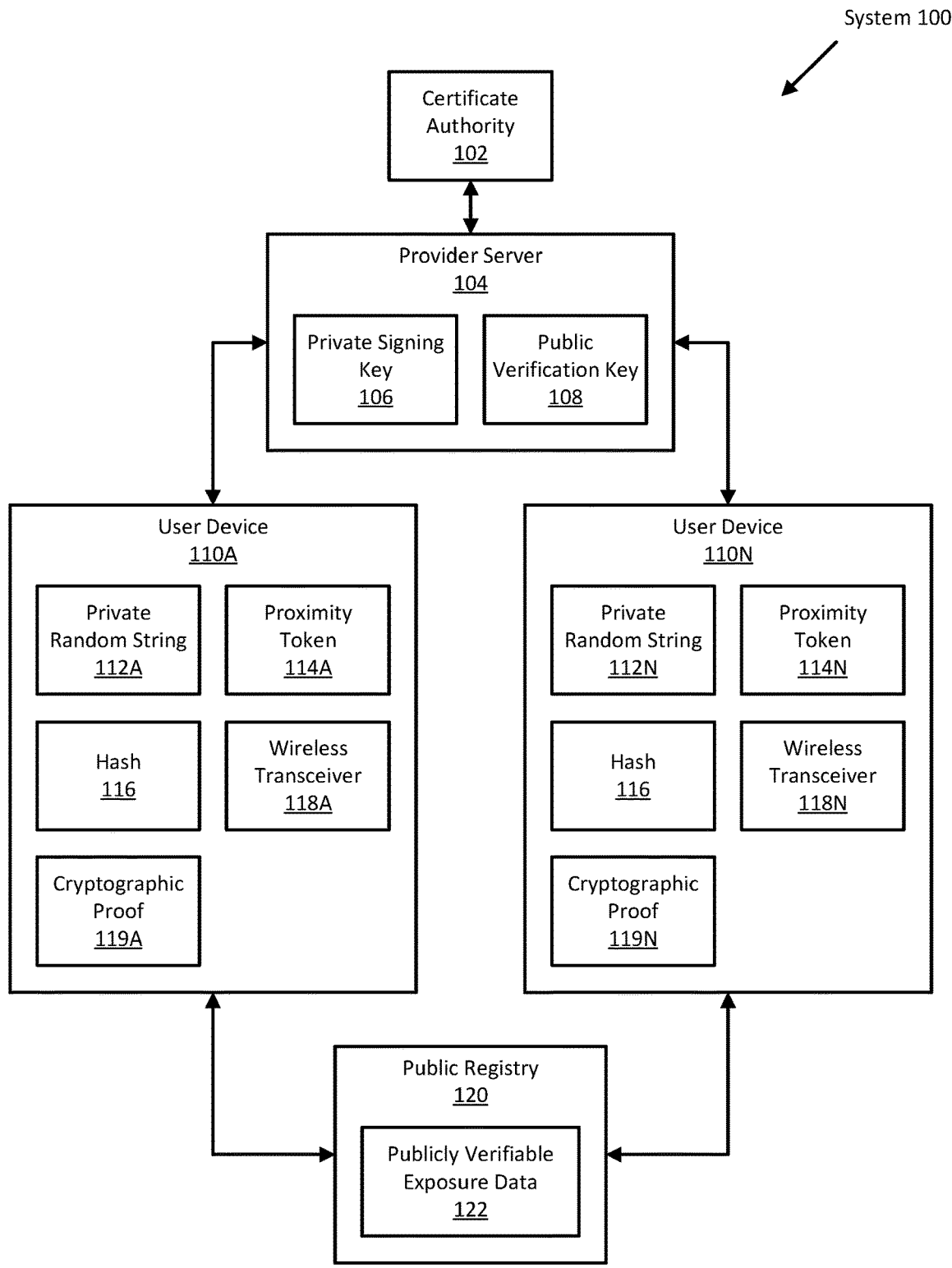
FIG. 1 is a block diagram of an example of a system according to an embodiment.

Techniques described herein allow for privacy-preserving contact tracing. An individual A who tests positive for a pathogen may furnish a cryptographic proof attesting to the following statements:

1. Individual A was in close proximity to individual B at some time t.
2. Individual A tested positive for the pathogen at time t'.
3. t' is within x days of t.

A produces and publishes the proof, and any individual may publicly verify the proof. In the example above, individual B may verify the proof and take appropriate action (e.g., seek testing) in a timely manner when the proof checks and reveals an exposure risk. Some or all of these operations may be performed in zero knowledge, i.e., without leaking information about A or B.

In addition, techniques described herein allow for nth-order contact tracing, i.e., identifying transitive exposure risk. Continuing the example above, using the first proof, individual B can then publish a cryptographic proof attesting to the fact that B was in close proximity to an individual who tested positive (in this case A), and that B was in close proximity to another individual C at $t'' \geq t + P_I$, where $P_I$ is the pathogen incubation period. Individual C may verify the proof and take appropriate action (e.g., seek testing) in a timely manner when the proof checks and reveals an exposure risk. Again, some or all of these operations may be performed in zero knowledge, i.e., without leaking information about A, B, or C. This approach may be extended to additional degrees of transitive exposure (e.g., $3^{rd}$ order, $4^{th}$ order, etc.).

As described in further detail below, one or more embodiments use zero-knowledge succinct non-interactive arguments of knowledge (zkSNARKs) as a cryptographic building block, and may be built on a decentralized approach (e.g., using Bluetooth® and/or another wireless technology) to allow clients to provide a cryptographic proof of proximity after a positive diagnosis. These cryptographic proofs are succinct, generally only a few hundred bytes, and very fast (e.g., on the order of just a few milliseconds) to verify. Succinct proofs may help promote adoption of contact tracing; for example, it may mitigate concerns about data usage when contact tracing is being performed using devices with data caps. The zero-knowledge property helps ensure that a person verifying these proofs learns their exposure risk (e.g., that they were close to someone who tested positive for the pathogen, or are n levels of contact removed from someone who tested positive for the pathogen), without learning (with some possible caveats discussed in further detail below) who the other individual(s) is/are and/or where the contact(s) occurred.

Techniques described herein allow for contact tracing that is faster and less labor-intensive than manual approaches, and that can therefore scale more effectively to larger populations. In addition, techniques described herein address privacy concerns associated with contact tracing, which can lead to more widespread adoption and increased efficacy of contact tracing technology. Nth-order contact tracing techniques described herein further improve the effectiveness of contact tracing by providing information about exposure risks beyond first-order contacts. Nth-order exposure risk is available in a timely manner through proof composition, with privacy being preserved by virtue of some or all of the operations being performed in zero knowledge.

One or more embodiments use an efficient preprocessing zkSNARK construction, performing signature verification outside the SNARK to reduce prover cost. In the case of nth-order exposure proofs, signature verification may occur inside the zkSNARK; however, one or more embodiments reduce circuit size by using an arithmetic circuit friendly digital signature scheme.

Techniques described herein may be performed without requiring any trusted third parties or databases. A public registry, as described herein, does not need not be trusted as long as there is a trusted setup (e.g., that a zkSNARK for the desired functionality is correctly set up).

One or more embodiments provide strong end-to-end privacy guarantees, because proximity tokens are not shared with third parties, healthcare providers, etc. In addition, correctness is assured because a valid proof guarantees the authenticity of the user's test results and the validity of the statement provided to the public repository.

A practical, privacy-preserving approach as described herein can help promote adoption of contact tracing technology. In an embodiment, a medical organization needs only to sign records using an existentially unforgeable and publicly verifiable signature scheme. This signing task is a simple one for the medical organization and deters malicious (noninfected) users from seeking signatures.

Using a decentralized approach as described herein, the burden is on the infected person to actually prove and publish. This approach allows better scaling (instead of requiring providers or third parties to centrally manage patient proximity data) and potentially better privacy since the user (the stakeholder) has full control over their private data and can share at will.

Some examples described herein refer to SARS-CoV-2 and COVID-19. These examples are for illustrative purposes only, and the techniques and embodiments should not be considered limited to contact tracing for SARS-CoV-2 and COVID-19.

Techniques described herein may be fully decentralized, requiring little assistance from the healthcare provider, and may be extended to support broader functionality.

II. System Architecture

FIG. 1 is a block diagram of an example of a system 100 according to an embodiment. In an embodiment, the system 100 may include more or fewer components than the components illustrated in FIG. 1. The components illustrated in FIG. 1 may be local to or remote from each other. The components illustrated in FIG. 1 may be implemented in software and/or hardware. Each component may be distributed over multiple applications and/or machines. Multiple components may be combined into one application and/or machine. Operations described with respect to one component may instead be performed by another component.

As illustrated in FIG. 1, the system 100 includes a provider server 104. The provider server 104 refers to hardware and/or software configured to perform some or all of trusted setup for privacy-preserving contact tracing. The provider server 104 is operated by and/or under control of a trusted entity, such as a healthcare provider or government organization. The provider server 104 is configured to generate a private signing key 106 and public verification key 108. The provider server 104 may further be configured to communicate with a certificate authority 102, to obtain a certificate for the private signing key 106.

The system 100 includes two or more user devices (e.g., user devices 110A, 100N). For ease of discussion, a user device 110A may be referred to herein simply as a "user." However, a "user" testing positive for a pathogen refers to an individual using the device. For example, "user A" testing positive for a pathogen and/or obtaining medical treatment refers to an individual using user device A (since a device cannot test positive for a pathogen). Wherever the term "user" refers to the performance of computational operations, it refers to the corresponding device.

Each user device 110A, 110N refers to hardware and/or software configured to perform operations described herein for privacy-preserving contact tracing. In general, a user device 110A, 110N may be any kind of device including a wireless receiver and a wireless transmitter, referred to collectively as a wireless transceiver 118A, 118N. For example, a user device 110A, 110N may be a smartphone, tablet, laptop computer, smart watch or other wearable device, fob, or other kind of device. Different user devices 110A, 110N may be different kinds of devices. The wireless transceivers 118A, 118N may be configured to operate using Bluetooth, Wi-Fi, audio signals, and/or another kind of wireless technology or combination thereof.

As described in further detail herein, the user devices 110A, 110N are configured to generate respective private random strings 112A, 112N. Using the private random strings 112A, 112N, the user devices 110A, 110N are further configured to generate respective proximity tokens 114A, 114N. The user devices 110A, 110N may each be configured to generate multiple proximity tokens 114A, 114N. For example, the user devices 110A, 110N may be configured to renew the proximity tokens 114A, 114N according to a predetermined schedule (e.g., every 5 minutes or according to another schedule), where the lifetime of a given proximity token 114A, 114N is referred to as an "epoch."

Contact tracing involves monitoring (by detecting and optionally measuring proximity) and recording physical interactions between individuals. To that end, the user devices 110A, 110N are configured to broadcast their respective proximity tokens 114A, 114N to each other using wireless transceivers 118A, 118N. As an example, if Alice (in this example, carrying user device 110A) walks into a cafe where Bob (in this example, carrying user device 110N) is eating, the user devices 110A, 110N may broadcast their respective proximity tokens 114A, 114N to each other. The user devices 110A, 110N may be configured to broadcast the proximity tokens 114A, 114N continuously, periodically, randomly, and/or according to another schedule. Each proximity token 110A, 110N may be valid for a particular epoch, after which the user devices 110A, 110N may be configured to generate new proximity tokens 114A, 114N.

Upon receiving proximity token 114N from user device 110N, user device 110A is configured to compute a hash 116 using both proximity tokens 114A, 114N. Upon receiving proximity token 114A from user device 110A, user device 110N is configured to compute the same hash 116 using both proximity tokens 114A, 114N. To ensure that the hash 116 is identical in both instances, the user devices 110A, 110N may be configured to sort the proximity tokens 114A, 114N (e.g., lexicographically) before generating the hash 116. Each user device 110A, 110N is configured to store the hash 116 for at least a predetermined amount of time (e.g., at least as long as the pathogen's incubation period).

If individual A, using user device 110A, test positive for the pathogen in question, the user device 110A is configured to generate a cryptographic proof 119A attesting to that fact. The cryptographic proof 119A may further attest to additional facts, as described in further detail below. The user device 110A may be configured to request a signature from the provider server 104 based on the private signing key 106. The user device 110A is configured to publish publicly verifiable exposure data 122 to a public registry 120, including at least (a) the cryptographic proof 119A, (b) the hash 116, and (c) the signature.

The public registry 120 is configured to store publicly verifiable exposure data 122 that other devices (e.g., user device 110N) can use to determine whether an exposure risk exists. For example, user device 110N may be configured to query the publicly verifiable exposure data 122 for the hash 116. If the publicly verifiable exposure data 122 includes the hash 116, that indicates that somebody (in this case, individual A) who came in contact with individual N (the user of user device 110N) tested positive for the pathogen and uploaded a cryptographic proof 119A to the public registry 120. User device 110N may be configured to verify the cryptographic proof 119A, using the provider server 104's public verification key 108. If the proof checks, then user device 110N has verified proof that the exposure occurred, and individual N can take appropriate action (e.g., seeking testing for the pathogen). A similar set of operations may be performed if individual N tests positive for the pathogen, with user device 110N generating a corresponding cryptographic proof 119N and uploading it to the public registry 120.

In an embodiment, the user devices 110A, 110N are further configured to perform operations described herein for nth-order privacy-preserving contact tracing, where n>1. The user devices 110A, 110N may thus be able to determine when transitive exposure to a pathogen has occurred, so that individuals can take appropriate action (e.g., seek testing). In general, nth-order privacy-preserving contact tracing extends the functionality of the system 100, as described above, to allow proofs of transitive exposure as described in further detail below.

In an embodiment, one or more components of the system 100 are implemented on one or more digital devices. The term "digital device" generally refers to any hardware device that includes a processor. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a hardware router, a hardware switch, a hardware firewall, a hardware network address translator (NAT), a hardware load balancer, a mainframe, a television, a content receiver, a set-top box, a printer, a mobile handset, a smartphone, a personal digital assistant ("PDA"), a wireless receiver and/or transmitter, a base station, a communication management device, a router, a switch, a controller, an access point, and/or a client device.

III. Example Operations for Privacy-Preserving Contact Tracing

Figure 2A:
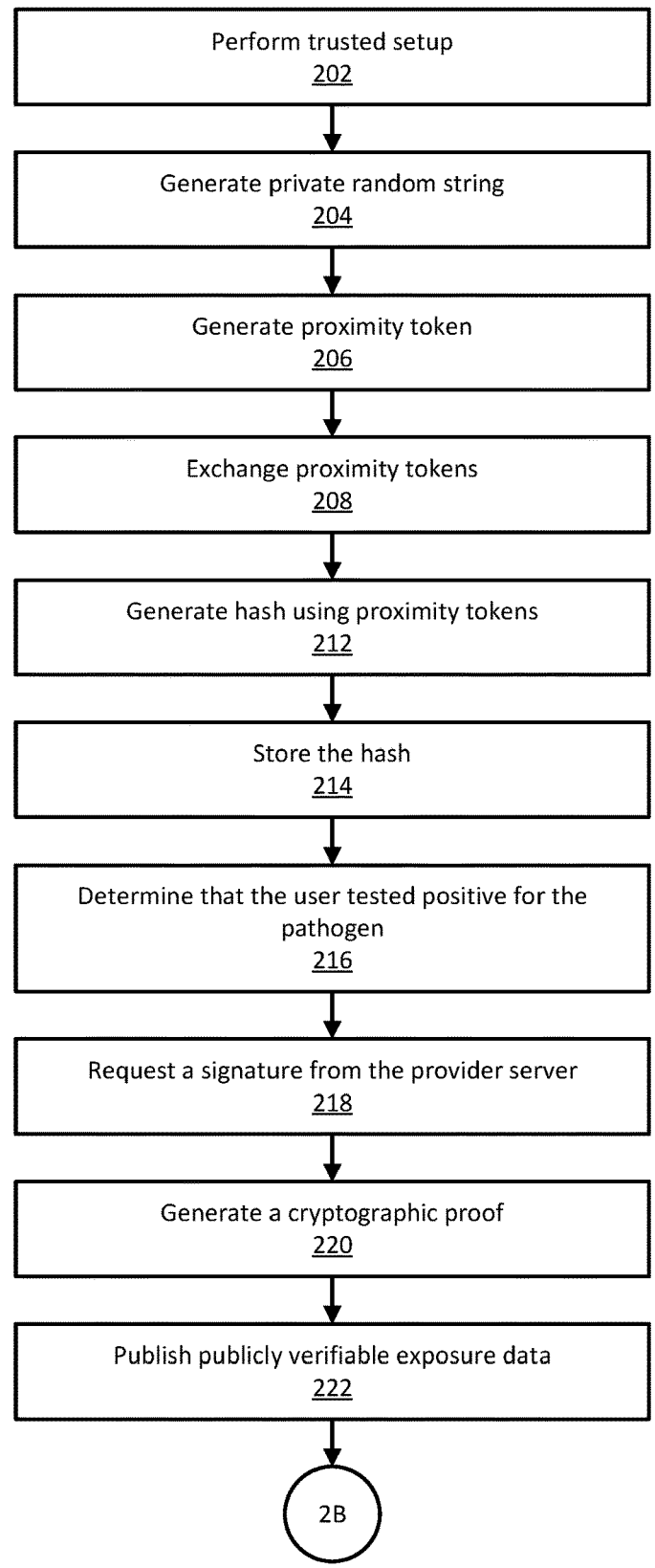
FIGS. 2A-2B are a flow diagram of an example of operations for privacy-preserving contact tracing according to an embodiment.
Figure 2B:
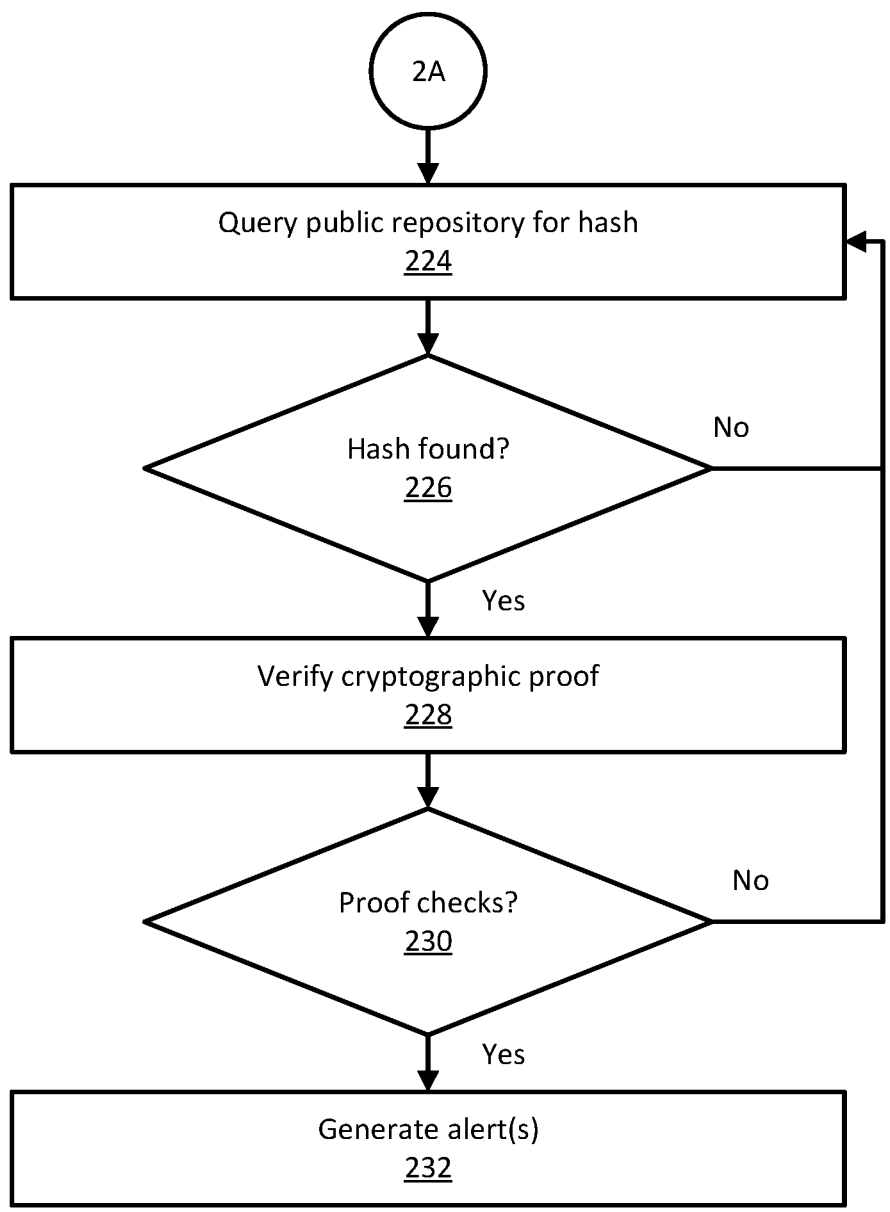

FIGS. 2A-2B are a flow diagram of an example of operations for privacy-preserving contact tracing according to an embodiment. One or more operations illustrated in FIGS. 2A-2B may be modified, rearranged, or omitted all together. Accordingly, the particular sequence of operations illustrated in FIGS. 2A-2B should not be construed as limiting the scope of one or more embodiments. Unless otherwise stated, operations described below are performed by one or more components of a system such as that illustrated in FIG. 1.

Initially, the system performs trusted setup (Operation 202). Trusted setup may include a provider server generating a private signing key and public verification key. The provider server may communicate with a certificate authority to obtain a certificate for the private signing key.

A user device generates a private random string (Operation 204) and uses the private random string to generate a proximity token (Operation 206). The user device then exchanges proximity tokens with another user device (Operation 208). To exchange proximity tokens, each user device may broadcast its respective proximity token and receive the other's proximity token. Each user device generates a hash using both proximity tokens (Operation 212) and stores the hash (Operation 214) for at least a predetermined amount of time (e.g., at least the incubation period of the pathogen in question).

In an embodiment, a user device determines that the corresponding individual (i.e., the user of the device) has tested positive for the pathogen (Operation 216). The individual may provide input to the user device indicating the positive test result and/or the user device may receive the test result from another device, such as from a healthcare provider. Responsive to determining that the individual tested positive, the user device requests a signature from the provider server (Operation 218) and generates a cryptographic proof 220 attesting to the positive test result. The user device publishes publicly verifiable exposure data to a public repository (Operation 222). The publicly verifiable exposure data includes at least the cryptographic proof and the hash of the proximity tokens, and may include additional information as described herein.

Turning to FIG. 2B, another user device queries the public repository (Operation 224) to determine whether the public repository contains any records linked to the hash(es) stored on that user device. A record linked to a hash stored on the user device indicates that another user device that exchanged proximity tokens with this user device uploaded a cryptographic proof of a positive test result, indicating an exposure risk. If the user device determines that one of its stored hash(es) is found in the public repository (Operation 226), then the user device verifies the cryptographic proof associated with that hash in the public repository (Operation 228). If the proof checks (Operation 230), then the user device generates one or more alerts (Operation 232). An alert indicates that an exposure to the pathogen occurred. The user device may present the alert (e.g., as a notification, sound, audio, etc.) to the user, so the user can take appropriate action (e.g., seeking testing). Alternatively or additionally, the user device may transmit an alert to a healthcare provider, government organization, and/or other trusted entity responsible for contact tracing.

As described herein, the operations described above may be extended to nth-order privacy-preserving contact tracing, in order to identify instances of transitive exposure.

Detailed examples are described in the sections below for purposes of clarity. Components and/or operations described below should be understood as examples that may not be applicable to one or more embodiments. Accordingly, components and/or operations described below should not be construed as limiting the scope of one or more embodiments.

IV. Preprocessing zkSNARK

As discussed above, one or more embodiments may use zkSNARKs for zero knowledge. Defining a preprocessing zkSNARK (pp-zk-SNARK) may include introducing arithmetic circuit satisfiability in Field F. An F-arithmetic circuit C: $F^n \times F^h \to F^l$ may be defined by the relation $R_C = \{(x,a): C(x,a) = 0^l\}$. Here, a is called the witness (auxiliary input), x is the public input, and the output is $0^l$. The language of the circuit may be defined by $L_C = \{x: \exists a, C(x,a) = 0^l\}$. Here, $x \in F^n$ (i.e., x is represented as n field elements), $a \in F^h$, and the output is $F^l$.

A hashing circuit may take, for example, the (private) input/witness a and its hash x, and assert that H(a)=x.

A preprocessing zkSNARK for F-arithmetic circuit satisfiability may include three algorithms (G, P, V), corresponding respectively to a Generator, a Prover, and a Verifier.

$G(\lambda, C) \to (pk, vk)$ Given a security parameter and the F-arithmetic circuit C, sample a keypair including a public proving key pk and a public verification key vk.

$P(pk, x, a) \to (\pi)$ Given the public prover key pk and any $(c, a) \in R_C$, generate a succinct proof $\pi$ attesting that $x \in L_C$.

$V(vk, x, \pi) \to b \in \{0, 1\}$ checks that $\pi$ is a valid proof for $x \in L_C$.

V. Proof-Carrying Data

In an embodiment, proof-carrying data (PCD) is used to capture one or more security guarantees for recursively composing zkSNARKs. Given a compliance predicate $\Pi$, a PCD system may check that a local computation involving a set of incoming messages $\vec{z}_{in}$, private local data $z_{loc}$, and outgoing message $z_{out}$, is $\Pi$-compliant.

Formally, a PCD system may include three polynomial-time algorithms (G, P, V) corresponding to a Generator, a Prover, and a Verifier.

$G(\lambda, \Pi) \to (pk, vk)$ Given a security parameter $\lambda$ and the compliance predicate $\Pi$ expressed as an F-arithmetic circuit, sample a keypair including a public proving key pk and a public verification key vk.

$P(pk, \vec{z}_{in}, \vec{\pi}_{in}, z_{loc}, z_{out}) \to (z_{out}, \pi_{out})$ Given the public prover key pk, a set of input messages $\vec{z}_{in}$ along with compliance proofs $\vec{\pi}_{in}$, local input $z_{loc}$, and output $z_{out}$, generate a succinct proof $\pi_{out}$ attesting that $z_{out}$ is $\Pi$-compliant.

$V(vk, z, \pi) \to b \in \{0, 1\}$ checks that $z_{out}$ is $\Pi$-compliant.

VI. Example Proof-of-Contact Protocol

The following is a non-limiting example of a proof-of-contact protocol. In this example, an existentially unforgeable signature scheme $S=(G_S, S_S, V_S)$ (e.g., elliptic curve digital signature algorithm (ECDSA)) has private signing key $v_s$ and public verification key $p_s$. Let H, $H_1$, $H_2$ be three collision-resistant hash functions, and let (G, P, V) be a pp-zk-SNARK. An example of a baseline protocol may then operate as follows:

1. In a trusted setup phase, a trusted entity may set up the system and run a generator algorithm $G(\lambda, C) \to (pk, vk)$. The circuit C is described in further detail below. During this phase, each healthcare provider may obtain a certificate for its respective signing key signed by a trusted certification authority.

2. Each user generates a private random string S.

3. User A generates a random token every time period t (i.e., each epoch, such as in 5-minute intervals or another time period) as $T_{A,t} = H_1(S, t)$, and frequently broadcasts the token. For ease of discussion, the time subscript is omitted hereafter wherever it is clear.

4. Upon receiving a proximity token from user B at time t, user A computes $h = H_2(T_A, T_B, t)$ and stores it for a predetermined amount of time (e.g., 14 days). User B computes the same output. To ensure the same output, tokens may be sorted (e.g., lexicographically or in some other consistent way) before passing them to the hash function.

5. In this example, user A tests positive for SARS-CoV-2 at time t', and obtains a "COVID.positive" test result from a medical provider. User A computes $h_s = H(S, COVID.positive, t')$ and requests signature $s = S_S(v_s, h_s)$ from the healthcare provider, where $v_s$ is the provider's private signing key. Note that user A does not have to reveal their secret S to the provider. User A may provide $h_s$ only, and a cryptographic proof that $h_s = H(S, COVID.positive, t')$ for some valid private witness S.

6. User A generates a short cryptographic proof using $P(pk, (h, h_s), (S, T_A, T_B, t')) \to \pi$ attesting to these facts:
   a. $h_s = H(S, COVID.positive, t')$
   b. $T_A = H_1(S, t)$
   c. $h = H_2(T_A, T_B, t)$
   d. $t' - t \leq 14$ days 7. User A publishes tuple $(\pi, h, h_s, s)$ to some public registry. To help prevent linkability, if the public registry already contains a tuple with the value h, then the user does not upload these values. In addition, various techniques may be used to help prevent network-based linkability. For example, the user's device may use mixing and/or onion routing solutions, the provider may publish the material on behalf of the user, and or another approach or combination thereof may be used.

8. User B checks the public registry periodically to find a matching h and can quickly verify the proof using V (vk, (h, $h_s$), π). If the proof checks, then user B verifies the signature $V_S(p_s, s, h_s)$, given $h_s$ and the public verification key $p_s$ of the healthcare provider.

9. User B seeks testing based on successful validation. If needed, user B may show the proof-of-contact to their healthcare provider to expedite the process.

VII. Security and Privacy

One or more embodiments described herein include one or more of the following security and privacy-protecting features.

1. Non-Linkability

In an embodiment, tokens are never shared (aside from the initial exchange between users) or published. Only the hash of two tokens is published after a user tests positive. Therefore, different tokens may not be linked as belonging to the same user. The same is true with linking different hashes. As described herein, when reporting a positive test, user A may publish $h=H_2(T_A, T_B, t)$ for all proximity edges. Only user B or some dishonest user C who forms a clique with A and B at time t may learn h. Since user C is part of the clique, h does not leak additional information. User C cannot use h to create valid proofs on behalf of A or B, without knowledge of their private strings S.

2. Identity Protection

In general, techniques describe herein protect individuals' identities by only publishing hashes without any personally identifying information. However, after seeing a proof containing h, a curious user B who keeps track of all physical encounters may a posteriori identify the infected person in some form. For example, if user B has only encountered one person before getting alerted, user B will be able to identify the infected person no matter how privacy-preserving the alert/protocol is. This may be acceptable in some cases. For example, there may be relatively little privacy risk in learning that the "tall person in the dairy aisle at the grocery store" (whose identity is unknown) tested positive. Alternatively, randomization techniques may be used to help protect the identities of diagnosed individuals. For example, a "parroting" approach may be used, such as that described in R. Canetti, Y. T. Kalai, A. Lysyanskaya, R. L. Rivest, A. Shamir, E. Shen, A. Trachtenberg, M. Varia, and D. J. Weitzner, "Privacy-preserving automated exposure notification," Cryptology ePrint Archive, Report 2020/863, 2020.

VIII. Transitive Exposure Proofs

As noted above, one or more embodiments allow for nth-order contact tracing, which allows for detecting transitive exposure to a pathogen. First-order contact tracing may not be fast enough to control the spread of a pathogen in a timely manner. For example, there may be a period of time in which individuals can be asymptomatic but contagious, and this period could be longer than the pathogen incubation period.

As an example, Alice may be asymptomatic but contagious at time $t_0$ and come in contact with Bob. Bob gets infected and comes in contact with Charlie at time $t_1 \geq t_0 + P_I$, where $P_I$ is the pathogen incubation period. Alice starts showing symptoms and tests positive at time $t_2 \geq t_1$, at which point Bob gets notified. Bob may not show symptoms, may wait to get tested, or may not even get tested. Even if Bob gets tested at time $t_3 > t_2$, there is a period of time (which could be several days) during which Charlie is not even aware of the exposure risk, and is going about his business as usual. Although Charlie did not directly come in contact with a carrier of the pathogen, he may find it useful to know that someone he came in contact with did.

Nth-order contact tracing may enable more informative statistics for users. For example, nth-order contact tracing may allow for the creation of an individual risk profile, i.e., a risk score based on how many degrees of exposure an individual has. Someone who is four transitive hops away from a pathogen carrier would generally be at lower risk than someone who is two hops away.

One example of an approach to extending a proof-of-contact protocol for transitive proofs operates as follows:

1. As in the first-order example discussed above, a trusted entity sets up the system and runs a generator algorithm $G(\lambda, C_2) \rightarrow (pk_2, vk_2)$. Here, $C_2$ is an additional circuit with corresponding prover and verifier keys $(pk_2, vk_2)$, for proving transitive exposure.

2. User B checks the public registry periodically to find a matching $h_i$ (from some user A who tested positive) and can quickly verify the proof using V (vk, $(h_i, h_s)$, π). If the proof checks, user B verifies the signature $V_S(p_s, s, h_s)$ given $h_s$ and the public verification key $p_s$ of the healthcare provider.

3. User B generates a short cryptographic proof using $P(pk_2, (h_i, h_j), (S, T_A, T_{B1}, T_{B2}, T_C)) \rightarrow \pi$, attesting to these facts:

a. $h_i = H_2(T_A, T_{B1}, t_1)$
  b. $h_j = H_2(T_{B2}, T_C, t_2)$
  c. $t_2 - t_1 \leq 3$ days 4. User B publishes tuple (π, $h_i$, $h_j$) to the public registry.

5. User C checks the public registry periodically to find a matching $h_j$ and can quickly verify the proof using V ($vk_2$, $(h_i, h_j)$, π). If the proof checks, user C can recursively verify the next proof in the chain until eventually arriving at the original proof. Finally, user C verifies the original proof using V (vk, $(h_i, h_s)$, π).

In this example, the zkSNARK includes the constraint $t_2 - t_1 \leq 3$, corresponding to the 3-day incubation period of Sars-CoV-2. In an embodiment, this parameter is configurable, for example, based on the pathogen in question, risk tolerances, emerging knowledge of a pathogen, etc. In general, the time when Bob comes in contact with Charlie should come after the time when Bob came in contact with Alice plus the incubation period. This approach reduces the number of false positives that would otherwise arise, such as if Bob alerted Charlie of 2nd-order exposure in a situation where Bob could not have possibly become contagious from Alice yet.

IX. Transitive Exposure Proofs Using Proof-Carrying Data

In some cases, contact tracing may suffer from a linkability vulnerability. For example, given uploaded ($h_i$, $h_j$) pairs, an adversary observing the public registry may deduce that whoever uploaded the tuple ($\pi_1$, $h_i$, $h_s$, s) must have come in contact with the person who uploaded the tuple ($\pi_2$, $h_i$, $h_j$), since $h_i$ is present in both tuples. Proof-carrying data (PCD) may be used to mitigate this vulnerability. Using PCD, previous proofs in the chain are verified and a proof that this verification was performed correctly is provided. The PCD system hides the details of intermediate proofs, while allowing a user to verify that the entire chain is valid. Instead of uploading the pairs ($h_i$, $h_j$), transitive proofs include single h values that are indistinguishable from random values.

As an example, for proof-of-contact, the compliance predicate Π may be represented as the signature verification algorithm $V_S(p_s, s, h_s)$, coupled with operations to prove that the randomness of $h_i$ is consistent with the randomness of some $h_j$. More formally, a user who tested positive may perform a Π-compliant computation $M_0$ that takes as input $z_{in}=(h_s, s, p_s)$, $z_{loc}=(S, t, t', T_A, T_{B1})$ and outputs $h_i$ satisfying the following constraints:

a. $h_s=H(S_A, \text{COVID.positive}, t')$
b. $T_A=H_1(S,t)$
c. $h_i=H_2(T_A, T_{B1}, t)$
d. $t'-t \leq 14$ days
e. $V_S(p_s, s, h_s)=1$ The user then uploads the value $h_i$ along with a cryptographic proof attesting that $M_0$ is H-compliant.

Figure 3:
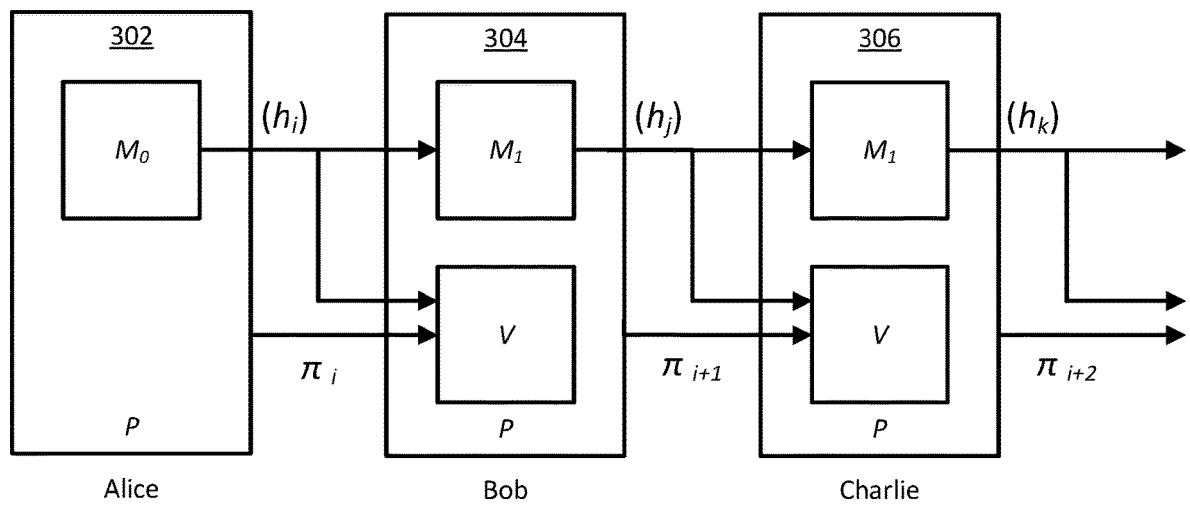
FIG. 3 is a block diagram of an example of a flow from proof-of-contact to proof of transitive exposure, according to an embodiment.

For proving transitive exposure, a user B who sees the value $h_i$ along with the PCD proof $\pi_i$ attesting to first-hand exposure may perform a Π-compliant computation $M_1$ that takes as input $z_{in}=(h_i, \pi_i)$, $z_{loc}(t_1, t_2, T_A, T_{B1}, T_{B2}, T_C)$ and outputs $h_j$ satisfying the following constraints:

a. $h_i=H_2(T_A, T_{B1}, t_1)$
b. $h_j=H_2(T_{B2}, T_C, t_2)$
c. $t_2-t_1 \leq 3$ days Additionally, user B may runs a verifier circuit over $\pi_i$ and provide a cryptographic proof that $V(vk, h_j, \pi_i)=1$ and $M_1$ is Π-compliant. FIG. 3 illustrates an example of a flow from proof-of-contact to proof of transitive exposure, according to an embodiment. In this example, Bob's device 304 is able to prove first-order contact with Alice's device 302; Charlie's device 306 is able to prove first-order contact with Bob's device 304 and second-order contact with Alice's device 302.

X. Proofs of Surface Transmission Via PCD

In some cases, contact tracing by measuring proximity between users may not be sufficient for effectively curbing the spread of a pathogen. A pathogen that lives for extended periods on surfaces could transmit from one user to another even though they have never been in close contact. For example, if a contagious user Alice sits on a park bench, then Bob, who visits the park the next day, may become infected from sitting on the same bench. If Alice tests positive, it would be preferable for users who are at risk from the surface spread of the pathogen be alerted.

One approach is to equip public and/or otherwise shared spaces (e.g., park benches, gas pumps, doorways, kitchens, bathrooms, etc.) with devices similar to the user devices discussed above (e.g., using Bluetooth transceivers), and have them participate in the contact tracing protocol. The devices could exchange tokens with users and verify proofs in a manner similar to the other user devices; the shared spaces could effectively be considered "users" for contact tracing purposes. After discovering a matching token in the public registry and verifying the corresponding proof, the device may upload a transitive proof of exposure, so that users may be alerted of the surface transmission risk.

Continuing the example above, rather than using PCD, a device associated with the park bench may upload its secondary tokens after a user Alice tests positive, i.e., the tokens exchanged with other users within 14 days of Alice's park visit. Although these users are alerted of surface contact risk, they must trust that the park bench device is acting honestly, since there is no way of verifying that Alice actually came in contact with the park bench. Alternatively, by using PCD, transitive proofs maintain the security and privacy guarantees from the single-hop (first order) contact tracing protocol.

XI. Anonymization of Network Traffic

In some cases, a passive adversary may have the ability to view a large portion of network traffic, and may be able to de-anonymize users as they interact with the public registry. For example, if a user uploads their proofs from a home router, an adversary may be able to determine which individual tested positive based on network traffic analysis alone. One or more embodiments use network anonymization techniques (e.g., Tor and/or other anonymization techniques) for efficient anonymization of the uploading/downloading of proofs. Alternatively or additionally, more stringent privacy guarantees may be used. For example, the kinds of protocols used in metadata-private messaging may be used.

XII. Trusted Setup

When dealing with a protocol where a trusted setup is needed (e.g., using pre-processing zero-knowledge SNARKs as described herein), there is a question of which entity should perform the trusted setup (generator) phase. One approach is for several community organizations to perform a secure multi-party computation (MPC) protocol. For example, the World Health Organization (WHO), Massachusetts General Hospital (MGH), and National Institute of Health (NIH) may jointly compute the trusted setup, and users would have high confidence in the system's security (that is, as long as they trust that these parties will not collude with one another). Alternatively, the system may be instantiated with a transparent zero-knowledge SNARK scheme. These zkSNARKs do not require a trusted setup, but require larger proof sizes.

XIII. Digital Signature Scheme

In an embodiment, providing nth-order exposure notifications requires encoding a digital signature scheme inside the compliance predicate. Without careful consideration of the scheme used, this can significantly increase the size of the compliance predicate, resulting in a prohibitive proving time. To address this concern, a Rivest-Shamir-Adleman (RSA) digital signature scheme may be used. For example, this scheme may be represented efficiently over $F_p$ by choosing public exponent $e=3$ and performing modular multiplication via radix $|\sqrt{p}|$ arithmetic.

XIV. Performance

In testing, a simplified proof-of-contact zkSNARK (without recursive composition) was implemented using the libsnark library. The library uses the NP-complete language R1CS to express the arithmetic circuits representing the zkSNARK. The libsnark library provides existing R1CS "gadgets" for functionality such as comparisons and collision-resistant hashing. Additionally, it includes an implementation of the subset-sum collision-resistant hashing gadget, which in this test was used as an efficient one-way hash.

Performance of a proof-of-contact zkSNARK may be characterized in terms of the running time and key sizes for both the prover and verifier (for example, as shown in Table 1). Since the generator phase is only executed once during setup, concrete numbers on the size of the arithmetic circuit (3060 gates) may be considered while effectively disregarding the time of the generator (166 ms). In this test, the circuit did not account for sorting.

Table 1, below, shows the performance of a test pp-zk-SNARK implementation, executed on a MacBook Pro with a 2.9 GHz Intel core i9 processor and 32 gigabytes (GB) of random access memory (RAM).

TABLE 1

|  | Prover | Verifier |
|---|---|---|
| Running time (milliseconds) | 65 | 9 |
| Key size (kilobytes) | 722 | 30 |

XV. General; Computer Systems; Networks

In an embodiment, a system includes one or more devices, including one or more hardware processors, that are configured to perform any of the operations described herein and/or recited in any of the claims.

In an embodiment, one or more non-transitory computer-readable storage media store instructions that, when executed by one or more hardware processors, cause performance of any of the operations described herein and/or recited in any of the claims.

Any combination of the features and functionalities described herein may be used in accordance with an embodiment. In the foregoing specification, embodiments have been described with reference to numerous specific details that may vary from implementation to implementation. Accordingly, the specification and figures are to be regarded in an illustrative rather than a restrictive sense. The sole and exclusive indicator of the scope of the invention, and what is intended by the Applicant to be the scope of the invention, is the literal and equivalent scope of the set of claims that issue from this application, in the specific form in which such claims issue, including any subsequent correction.

In an embodiment, techniques described herein are implemented by one or more special-purpose computing devices (i.e., computing devices specially configured to perform certain functionality). The special-purpose computing device(s) may be hard-wired to perform the techniques and/or may include digital electronic devices such as one or more application-specific integrated circuits (ASICs), field programmable gate arrays (FPGAs), and/or network processing units (NPUs) that are persistently programmed to perform the techniques. Alternatively or additionally, a computing device may include one or more general-purpose hardware processors programmed to perform the techniques pursuant to program instructions in firmware, memory, and/or other storage. Alternatively or additionally, a special-purpose computing device may combine custom hard-wired logic, ASICs, FPGAs, or NPUs with custom programming to accomplish the techniques. A special-purpose computing device may include a desktop computer system, portable computer system, handheld device, networking device, and/or any other device(s) incorporating hard-wired and/or program logic to implement the techniques.

Figure 4:
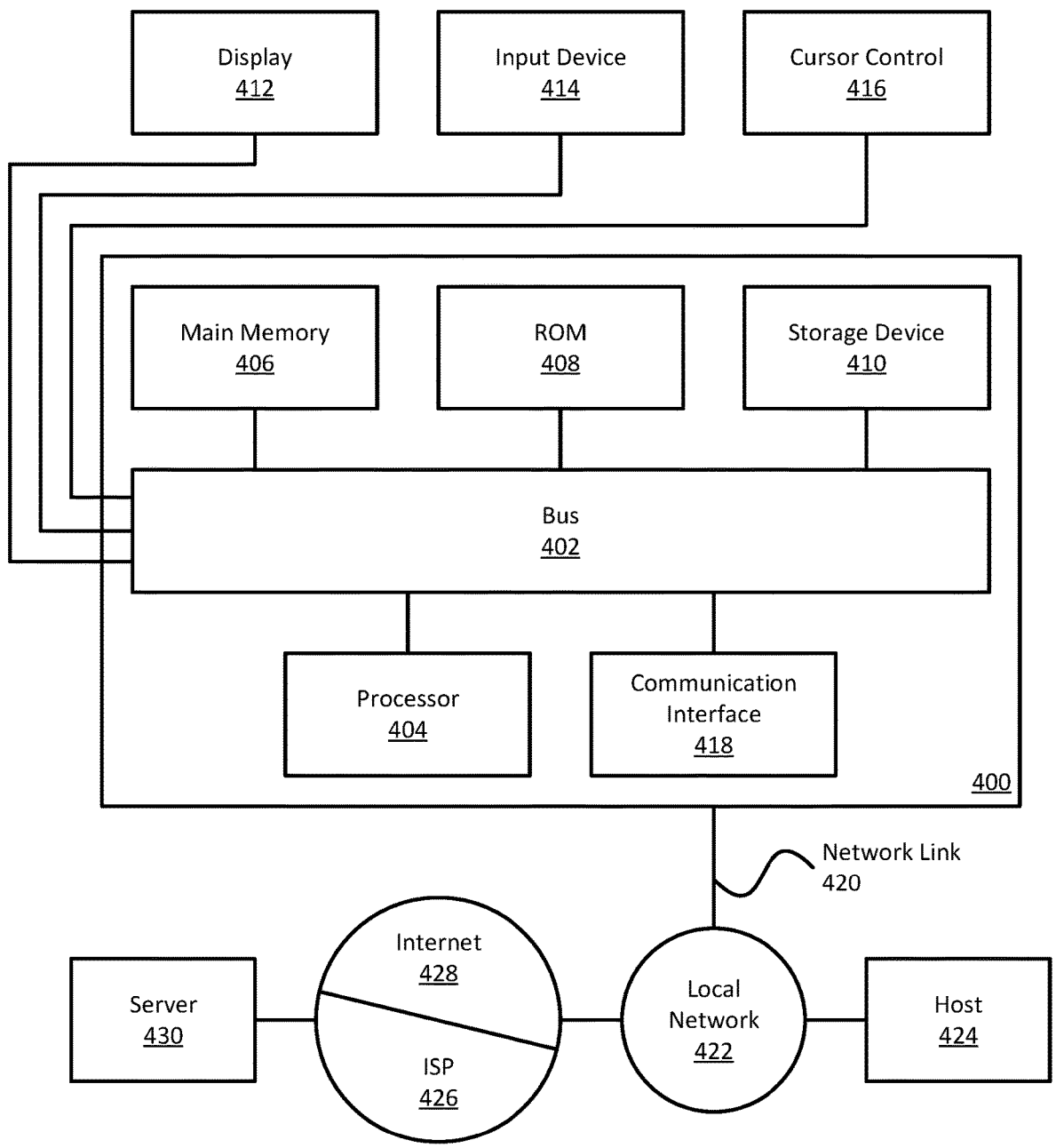
FIG. 4 is a block diagram of an example of a computer system according to an embodiment.

For example, FIG. 4 is a block diagram of an example of a computer system 400 according to an embodiment. Computer system 400 includes a bus 402 or other communication mechanism for communicating information, and a hardware processor 404 coupled with the bus 402 for processing information. Hardware processor 404 may be a general-purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in one or more non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk or optical disk, is provided and coupled to bus 402 for storing information and instructions.

Computer system 400 may be coupled via bus 402 to a display 412, such as a liquid crystal display (LCD), plasma display, electronic ink display, cathode ray tube (CRT) monitor, or any other kind of device for displaying information to a computer user. An input device 414, including alphanumeric and other keys, may be coupled to bus 402 for communicating information and command selections to processor 404. Alternatively or additionally, computer system 400 may receive user input via a cursor control 416, such as a mouse, a trackball, a trackpad, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane. Alternatively or additionally, computer system 4 may include a touchscreen. Display 412 may be configured to receive user input via one or more pressure-sensitive sensors, multi-touch sensors, and/or gesture sensors. Alternatively or additionally, computer system 400 may receive user input via a microphone, video camera, and/or some other kind of user input device (not shown).

Computer system 400 may implement the techniques described herein using customized hard-wired logic, one or more ASICs or FPGAs, firmware, and/or program logic which in combination with other components of computer system 400 causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. Alternatively or additionally, hard-wired circuitry may be used in place of or in combination with software instructions.

The term "storage media" as used herein refers to one or more non-transitory media storing data and/or instructions that cause a machine to operate in a specific fashion. Such storage media may comprise non-volatile media and/or volatile media. Non-volatile media includes, for example, optical or magnetic disks, such as storage device 410. Volatile media includes dynamic memory, such as main memory 406. Common forms of storage media include, for example, a floppy disk, a flexible disk, hard disk, solid state drive, magnetic tape or other magnetic data storage medium, a CD-ROM or any other optical data storage medium, any physical medium with patterns of holes, a RAM, a programmable read-only memory (PROM), an erasable PROM (EPROM), a FLASH-EPROM, non-volatile random-access memory (NVRAM), any other memory chip or cartridge, content-addressable memory (CAM), and ternary content-addressable memory (TCAM).

A storage medium is distinct from but may be used in conjunction with a transmission medium. Transmission media participate in transferring information between storage media. Examples of transmission media include coaxial cables, copper wire, and fiber optics, including the wires that comprise bus 402. Transmission media may also take the form of acoustic or light waves, such as those generated during radio-wave and infra-red data communications.

Various forms of media may be involved in carrying one or more sequences of one or more instructions to processor 404 for execution. For example, the instructions may initially be carried on a magnetic disk or solid state drive of a remote computer. The remote computer may load the instructions into its dynamic memory and send the instructions over a network, via a network interface controller (NIC), such as an Ethernet controller or Wi-Fi controller. A NIC local to computer system 400 may receive the data from the network and place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422, and communication interface 418.

The received code may be executed by processor 404 as it is received, and/or stored in storage device 410, or other non-volatile storage for later execution.

In an embodiment, a computer network provides connectivity among a set of nodes running software that utilizes techniques as described herein. The nodes may be local to and/or remote from each other. The nodes are connected by a set of links. Examples of links include a coaxial cable, an unshielded twisted cable, a copper cable, an optical fiber, and a virtual link.

A subset of nodes implements the computer network. Examples of such nodes include a switch, a router, a firewall, and a network address translator (NAT). Another subset of nodes uses the computer network. Such nodes (also referred to as "hosts") may execute a client process and/or a server process. A client process makes a request for a computing service (for example, a request to execute a particular application and/or retrieve a particular set of data). A server process responds by executing the requested service and/or returning corresponding data.

A computer network may be a physical network, including physical nodes connected by physical links. A physical node is any digital device. A physical node may be a function-specific hardware device. Examples of function-specific hardware devices include a hardware switch, a hardware router, a hardware firewall, and a hardware NAT. Alternatively or additionally, a physical node may be any physical resource that provides compute power to perform a task, such as one that is configured to execute various virtual machines and/or applications performing respective functions. A physical link is a physical medium connecting two or more physical nodes. Examples of links include a coaxial cable, an unshielded twisted cable, a copper cable, and an optical fiber.

A computer network may be an overlay network. An overlay network is a logical network implemented on top of another network (for example, a physical network). Each node in an overlay network corresponds to a respective node in the underlying network. Accordingly, each node in an overlay network is associated with both an overlay address (to address the overlay node) and an underlay address (to address the underlay node that implements the overlay node). An overlay node may be a digital device and/or a software process (for example, a virtual machine, an application instance, or a thread). A link that connects overlay nodes may be implemented as a tunnel through the underlying network. The overlay nodes at either end of the tunnel may treat the underlying multi-hop path between them as a single logical link. Tunneling is performed through encapsulation and decapsulation.

In an embodiment, a client may be local to and/or remote from a computer network. The client may access the computer network over other computer networks, such as a private network or the Internet. The client may communicate requests to the computer network using a communications protocol, such as Hypertext Transfer Protocol (HTTP). The requests are communicated through an interface, such as a client interface (such as a web browser), a program interface, or an application programming interface (API).

In an embodiment, a computer network provides connectivity between clients and network resources. Network resources include hardware and/or software configured to execute server processes. Examples of network resources include a processor, a data storage, a virtual machine, a container, and/or a software application. Network resources may be shared amongst multiple clients. Clients request computing services from a computer network independently of each other. Network resources are dynamically assigned to the requests and/or clients on an on-demand basis. Network resources assigned to each request and/or client may be scaled up or down based on, for example, (a) the computing services requested by a particular client, (b) the aggregated computing services requested by a particular tenant, and/or (c) the aggregated computing services requested of the computer network. Such a computer network may be referred to as a "cloud network."

In an embodiment, a service provider provides a cloud network to one or more end users. Various service models may be implemented by the cloud network, including but not limited to Software-as-a-Service (SaaS), Platform-as-a-Service (PaaS), and Infrastructure-as-a-Service (IaaS). In SaaS, a service provider provides end users the capability to use the service provider's applications, which are executing on the network resources. In PaaS, the service provider provides end users the capability to deploy custom applications onto the network resources. The custom applications may be created using programming languages, libraries, services, and tools supported by the service provider. In IaaS, the service provider provides end users the capability to provision processing, storage, networks, and other fundamental computing resources provided by the network resources. Any applications, including an operating system, may be deployed on the network resources.

In an embodiment, various deployment models may be implemented by a computer network, including but not limited to a private cloud, a public cloud, and a hybrid cloud. In a private cloud, network resources are provisioned for exclusive use by a particular group of one or more entities (the term "entity" as used herein refers to a corporation, organization, person, or other entity). The network resources may be local to and/or remote from the premises of the particular group of entities. In a public cloud, cloud resources are provisioned for multiple entities that are independent from each other (also referred to as "tenants" or "customers"). In a hybrid cloud, a computer network includes a private cloud and a public cloud. An interface between the private cloud and the public cloud allows for data and application portability. Data stored at the private cloud and data stored at the public cloud may be exchanged through the interface. Applications implemented at the private cloud and applications implemented at the public cloud may have dependencies on each other. A call from an application at the private cloud to an application at the public cloud (and vice versa) may be executed through the interface.

In an embodiment, a system supports multiple tenants. A tenant is a corporation, organization, enterprise, business unit, employee, or other entity that accesses a shared computing resource (for example, a computing resource shared in a public cloud). One tenant (through operation, tenant-specific practices, employees, and/or identification to the external world) may be separate from another tenant. The computer network and the network resources thereof are accessed by clients corresponding to different tenants. Such a computer network may be referred to as a "multi-tenant computer network." Several tenants may use a same particular network resource at different times and/or at the same time. The network resources may be local to and/or remote from the premises of the tenants. Different tenants may demand different network requirements for the computer network. Examples of network requirements include processing speed, amount of data storage, security requirements, performance requirements, throughput requirements, latency requirements, resiliency requirements, Quality of Service (QoS) requirements, tenant isolation, and/or consistency. The same computer network may need to implement different network requirements demanded by different tenants.

In an embodiment, in a multi-tenant computer network, tenant isolation is implemented to ensure that the applications and/or data of different tenants are not shared with each other. Various tenant isolation approaches may be used. In an embodiment, each tenant is associated with a tenant ID. Applications implemented by the computer network are tagged with tenant ID's. Additionally or alternatively, data structures and/or datasets, stored by the computer network, are tagged with tenant ID's. A tenant is permitted access to a particular application, data structure, and/or dataset only if the tenant and the particular application, data structure, and/or dataset are associated with a same tenant ID. As an example, each database implemented by a multi-tenant computer network may be tagged with a tenant ID. Only a tenant associated with the corresponding tenant ID may access data of a particular database. As another example, each entry in a database implemented by a multi-tenant computer network may be tagged with a tenant ID. Only a tenant associated with the corresponding tenant ID may access data of a particular entry. However, the database may be shared by multiple tenants. A subscription list may indicate which tenants have authorization to access which applications. For each application, a list of tenant ID's of tenants authorized to access the application is stored. A tenant is permitted access to a particular application only if the tenant ID of the tenant is included in the subscription list corresponding to the particular application.

In an embodiment, network resources (such as digital devices, virtual machines, application instances, and threads) corresponding to different tenants are isolated to tenant-specific overlay networks maintained by the multi-tenant computer network. As an example, packets from any source device in a tenant overlay network may only be transmitted to other devices within the same tenant overlay network. Encapsulation tunnels may be used to prohibit any transmissions from a source device on a tenant overlay network to devices in other tenant overlay networks. Specifically, the packets, received from the source device, are encapsulated within an outer packet. The outer packet is transmitted from a first encapsulation tunnel endpoint (in communication with the source device in the tenant overlay network) to a second encapsulation tunnel endpoint (in communication with the destination device in the tenant overlay network). The second encapsulation tunnel endpoint decapsulates the outer packet to obtain the original packet transmitted by the source device. The original packet is transmitted from the second encapsulation tunnel endpoint to the destination device in the same particular overlay network.

What is claimed is:

1. One or more non-transitory computer-readable media storing instructions that, when executed by one or more processors, cause the one or more processors to perform operations comprising:
generating, by a first user device, a first proximity token for contact tracing;
receiving, by the first user device, a second proximity token from a second user device;
generating, by the first user device, a first hash based on the first proximity token and the second proximity token;
generating, by the first user device using a prover function of a preprocessing zero knowledge succinct non-interactive argument of knowledge (pp-zk-SNARK), a first cryptographic proof attesting that a first individual associated with the first user device tested positive for a pathogen;
transmitting, by the first user device, first publicly verifiable exposure data comprising at least the first cryptographic proof and the first hash to a public registry;
generating, by a third user device, a second hash based on proximity tokens from the third user device and a fourth user device;
checking, by the third user device, a second cryptographic proof using a verifier function of the pp-zk-SNARK, the second cryptographic proof attesting that a third individual associated with a fifth user device had (N-1)th-order contact with the first individual who tested positive for a pathogen; and based at least on checking the second cryptographic proof, determining, by the third user device, that a fourth individual associated with the third user device had Nth-order contact with the pathogen;

generating, by the third user device using the prover function of the pp-zk-SNARK, a third cryptographic proof attesting that the fourth individual associated with the third user device had an Nth-order exposure to the pathogen, the third cryptographic proof being a transitive privacy-preserving proof hiding details of intermediate proofs; and transmitting, by the third user device, second publicly verifiable exposure data comprising at least the fourth cryptographic proof and the second hash to the public registry.

2. The one or more non-transitory computer-readable media of claim 1, the operations further comprising:
receiving, by the second user device, the first proximity token from the first user device;
generating, by the second user device, the first hash based on the first proximity token and the second proximity token;
determining, by the second user device, that the public registry comprises the first hash;
responsive to determining that the public registry comprises the first hash, checking the first cryptographic proof using the verifier function of the pp-zk-SNARK; and
based at least on checking the first cryptographic proof, determining that a second individual associated with the second user device had contact with the first individual.

3. The one or more non-transitory computer-readable media of claim 2, the operations further comprising:
generating an alert indicating that the second user device had contact with the first individual.

4. The one or more non-transitory computer-readable media of claim 1, the operations further comprising:
obtaining, by the first user device, a signature based on a private signing key from a healthcare provider, the first publicly verifiable exposure data further comprising the signature.

5. The one or more non-transitory computer-readable media of claim 1, the second user device being associated with a shared space and used for surface-based contact tracing.

6. A system comprising:
at least one device including a hardware processor;
the system being configured to perform operations comprising:
generating, by a first user device, a first proximity token for contact tracing;
receiving, by the first user device, a second proximity token from a second user device;
generating, by the first user device, a first hash based on the first proximity token and the second proximity token;
generating, by the first user device using a prover function of a preprocessing zero knowledge succinct non-interactive argument of knowledge (pp-zk-SNARK), a first cryptographic proof attesting that a first individual associated with the first user device tested positive for a pathogen;

transmitting, by the first user device, first publicly verifiable exposure data comprising at least the first cryptographic proof and the first hash to a public registry;

generating, by a third user device, a second hash based on proximity tokens from the third user device and a fourth user device;

checking, by the third user device, a second cryptographic proof using a verifier function of the pp-zk-SNARK, the second cryptographic proof attesting that a third individual associated with a fifth user device had (N-1)th-order contact with the first individual who tested positive for a pathogen; and based at least on checking the second cryptographic proof, determining, by the third user device, that a fourth individual associated with the third user device had Nth-order contact with the pathogen;

generating, by the third user device using the prover function of the pp-zk-SNARK, a third cryptographic proof attesting that the fourth individual associated with the third user device had an Nth-order exposure to the pathogen, the third cryptographic proof being a transitive privacy-preserving proof hiding details of intermediate proofs; and transmitting, by the third user device, second publicly verifiable exposure data comprising at least the fourth cryptographic proof and the second hash to the public registry.

7. The system of claim 6, the operations further comprising:
receiving, by the second user device, the first proximity token from the first user device;
generating, by the second user device, the first hash based on the first proximity token and the second proximity token;
determining, by the second user device, that the public registry comprises the first hash;
responsive to determining that the public registry comprises the first hash, checking the first cryptographic proof using the verifier function of the pp-zk-SNARK; and
based at least on checking the first cryptographic proof, determining that a second individual associated with the second user device had contact with the first individual.

8. The system of claim 7, the operations further comprising:
generating an alert indicating that the second user device had contact with the first individual.

9. The system of claim 6, the operations further comprising:
obtaining, by the first user device, a signature based on a private signing key from a healthcare provider, the first publicly verifiable exposure data further comprising the signature.

10. The system of claim 6, the second user device being associated with a shared space and used for surface-based contact tracing.

11. A method comprising:
generating, by a first user device, a first proximity token for contact tracing;
receiving, by the first user device, a second proximity token from a second user device;
generating, by the first user device, a first hash based on the first proximity token and the second proximity token;

generating, by the first user device using a prover function of a preprocessing zero knowledge succinct non-interactive argument of knowledge (pp-zk-SNARK), a first cryptographic proof attesting that a first individual associated with the first user device tested positive for a pathogen;

transmitting, by the first user device, first publicly verifiable exposure data comprising at least the first cryptographic proof and the first hash to a public registry;

generating, by a third user device, a second hash based on proximity tokens from the third user device and a fourth user device;

checking, by the third user device, a second cryptographic proof using a verifier function of the pp-zk-SNARK, the second cryptographic proof attesting that a third individual associated with a fifth user device had (N-1)th-order contact with the first individual who tested positive for a pathogen; and based at least on checking the second cryptographic proof, determining, by the third user device, that a fourth individual associated with the third user device had Nth-order contact with the pathogen;

generating, by the third user device using the prover function of the pp-zk-SNARK, a third cryptographic proof attesting that the fourth individual associated with the third user device had an Nth-order exposure to the pathogen, the third cryptographic proof being a transitive privacy-preserving proof hiding details of intermediate proofs; and transmitting, by the third user device, second publicly verifiable exposure data comprising at least the fourth cryptographic proof and the second hash to the public registry.

12. The method of claim 11, further comprising:

receiving, by the second user device, the first proximity token from the first user device;

generating, by the second user device, the first hash based on the first proximity token and the second proximity token;

determining, by the second user device, that the public registry comprises the first hash;

responsive to determining that the public registry comprises the first hash, checking the first cryptographic proof using the verifier function of the pp-zk-SNARK; and based at least on checking the first cryptographic proof, determining that a second individual associated with the second user device had contact with the first individual.

13. The method of claim 11, further comprising:

obtaining, by the first user device, a signature based on a private signing key from a healthcare provider, the first publicly verifiable exposure data further comprising the signature.

14. The method of claim 11, the second user device being associated with a shared space and used for surface-based contact tracing.

* * * * *